United States Patent [19]
Ansari et al.

[11] Patent Number: 6,165,443
[45] Date of Patent: *Dec. 26, 2000

[54] METHOD FOR VISUALLY DEMONSTRATING THE EFFECTIVENESS OF AN ANTIBACTERIA ATTACHMENT COMPOSITION

[75] Inventors: Shamim Alam Ansari, Princeton; Diana Kalliope Kiozpeoplou-Grina, Neshanic Station; Thomas Gregory Polefka, Somerset, all of N.J.

[73] Assignee: Colgate-Palmolive Company, New York, N.Y.

[ * ] Notice: This patent is subject to a terminal disclaimer.

[21] Appl. No.: 09/363,898

[22] Filed: Jul. 30, 1999

Related U.S. Application Data

[63] Continuation-in-part of application No. 09/141,904, Aug. 28, 1998, Pat. No. 5,951,965.

[51] Int. Cl.[7] .............................. A61B 10/00; A61B 5/00; A61B 8/00
[52] U.S. Cl. ......................... 424/9.8; 424/1.11; 424/9.1; 510/130
[58] Field of Search ................................. 424/1.11, 9.1, 424/9.8; 510/130, 131, 140, 535; 604/19; 556/465; 528/12; 435/252.3

[56] References Cited

U.S. PATENT DOCUMENTS

| | | | |
|---|---|---|---|
| 4,812,253 | 3/1989 | Small et al. | 252/132 |
| 5,460,800 | 10/1995 | Walters | 424/9.6 |
| 5,789,191 | 8/1998 | Mayer et al. | 435/39 |
| 5,951,965 | 9/1999 | Ansari et al. | 424/9.8 |

FOREIGN PATENT DOCUMENTS

| | | | |
|---|---|---|---|
| 0561489A2 | 1/1993 | European Pat. Off. | A61K 7/32 |
| WO95/04156 | 2/1995 | European Pat. Off. | C12Q 1/04 |
| 2136445A | 3/1984 | United Kingdom | C11D 10/02 |

*Primary Examiner*—Dameron Jones
*Attorney, Agent, or Firm*—Martin B. Barancik

[57] ABSTRACT

A method for visually demonstrating the effectiveness of an anti-bacteria attachment composition which comprises:

a. treating skin with potential or known anti-bacteria attachment composition;
b. contacting the said skin with a bacteria, resulting in the skin having bacteria attached to it;
c. contacting the skin with a bacteria growth supporting medium having optionally therein or later optionally added a compound or mixture thereof which will assist in visually detecting a bacterial colony.

10 Claims, No Drawings

METHOD FOR VISUALLY DEMONSTRATING THE EFFECTIVENESS OF AN ANTIBACTERIA ATTACHMENT COMPOSITION

This application is a Continuation-in-Part of prior application U.S. Ser. No. 09/141,904 filed Aug. 28, 1998 now U.S. Pat. No. 5,951,965, the disclosure of which is incorporated herein by reference.

BACKGROUND OF THE INVENTION

The washing of human skin with cleansing formulations has been associated with the removal of bacteria for over one hundred years. However, neither the qualitative nor quantitative effectiveness of skin cleanser in bacteria removal has been readily visually demonstrated to the skin cleansing public. Radiolabelling of bacteria and counting amounts of radiolabel left on skin samples is certainly an unacceptable method.

In like manner, there may be a growing interest in preventing attachment of bacteria to various body cells. A document is directed to inhibiting adhesion of a strep pyogenes to specific cells located in the oral cavity, U.S. Pat. No. 5,002,759. Another document, U.S. Pat. No. 5,683,991 is specifically directed to inhibiting *E. Coli* attachment to epithelial cells of the gastrointestinal tract and urogenital tract through the use of specific galacturonides. EP 806935 A is directed to the use of a carbohydrate or derivative thereof as an antiadhesive against a host of harmful materials including bacteria, parasites and protozoa on cell surfaces such as skin, mucous membranes, body orifices, interiors or hollow body organs, wounds, eyes and hair. U.S. Pat. No. 5,416,075 discloses the use of an oil in water emulsion having an amphipathic molecule including a biospecific moiety at the head end of its hydrophilic part. These compositions are applied to the skin. These headgroups inhibit adhesion of bacteria to the skin.

However, there is no rapid visual demonstration of the efficacy of such a process.

Such a method has now been discovered. It is rapid. It visually demonstrates the efficacy of any such effective or purportedly effective composition. Furthermore, it is effective for a large cross section of bacteria which can be transmitted to the skin.

SUMMARY OF THE INVENTION

In accordance with the invention there is a method for visually demonstrating the effectiveness of an anti-bacteria attachment composition which comprises:

a. treating skin with a potential or known inhibition of bacteria attachment composition;

b. contacting the said skin with a bacteria resulting in the skin having the bacteria attached to it;

c. contacting the skin with a bacteria growth supporting medium having optionally therein or optionally later added a compound or mixture thereof which will assist in visually detecting a bacterial colony.

It should be noted that most people can usually detect a colony of bacteria growing on an agar plate or other supporting media and readily successfully compare a medium with heavy bacterial growth to a medium with light to moderate bacterial growth. Certain bacteria can be visually detectable as a colored grouping without a separate visually detectable medium applied to it. Such bacteria include *Serratia marcescens, Straphylococcus aureus, Pseudomonas fluorescens, Pseudomonas aeroginosa, Bacteroides asaccharolyticus* and *bacteroides melaninogenicus*.

However, frequently bacterial growth media have certain component(s) therein which will specifically support the growth of certain bacteria and provide a readily visible color to the bacteria. Furthermore there are certain compound(s) available which when added to the growth media will selectively color certain bacteria, even in the presence of other bacteria.

A further aspect of the invention is a method of visually evaluating the comparable effectiveness of potential or known inhibition of bacteria attachment compositions which comprises steps a, b and c above for each bacteria attachment composition being evaluated and comparing the visual quantities of bacteria colonies on the skin for each said composition

DETAILED DESCRIPTION OF THE INVENTION

Examples of bacteria which are inhibited from attaching to the skin include *Staphylococcus aureus, Staphylococcus epidermidis, Corynebacterium minutissimum, Escherichia coli, Salmonella choleraesuis* and *Serratia marcescens* as well as other bacteria mentioned in this application.

The test is simple to run and provides an easy method of assessing visible quantity of bacteria on the skin. A skin part, including but not limited to an ex vivo skin explant or any source from animal and human, synthetic skin and the like, for example the hand, is contacted with a test composition which may inhibit bacteria attachment. On a similar part of the skin, a control composition is applied that does not have the component(s) of the test composition which allegedly bring about the inhibition of bacteria attachment. For example a soap composition having inhibitors of bacteria attachment is applied to the skin (hand). On the other hand the same soap composition without the component(s) responsible for inhibition of bacteria attachment is applied. Each hand is now contacted with a specific bacterium or various bacteria against which the inhibition of bacteria attachment composition is thought to be effective. After a period of time, the hand is contacted with a bacteria growth supporting solid medium which will support bacteria growth or a medium to which the bacterial growth nutrient can be readily added. An example of a growth support medium is agar. Incorporated within the medium or added an appropriate time thereafter is an amount of growth nutrient in sufficient quantity to bring about the growth of the various bacteria transferred from the skin. After an appropriate period of time to allow growth to occur, at least partially dependent on the temperature, particular bacteria, and the like, the medium bearing the bacteria is visually assessed.

As stated previously, individuals with normal vision are able to visualize the bacterial colonies and can distinguish between various levels of growth, such as high and moderate. This is without any additional visual effect that is, bacteria without any natural color. As noted previously, some bacteria do have a natural color. Additionally, color can be imparted to bacterial colonies by the nature of the nutrient growth material employed since many bacteria are capable of producing pigments when grown in medium supplemented with specific nutrients. Such medium can be selective or differential in nature. For example, such nutrient medium will bring about color pigment for the following bacteria:

*Escherichia coli* will produce colony with a characteristic green metallic sheen on agar containing Eosin Methylene Blue. Such nutrient medium can include such components as peptone, lactose, dipotassium hydrogen phosphate, Eosin Y, Methylene Blue and agar at a pH of 6.8.

*Staphylococcus aureus* will produce colony with a characteristic yellow color when grown on mannitol salt agar. Such nutrient medium can include the following components per liter of purified water:

| | |
|---|---|
| Pancreatic digest of Casein | 5.0 g |
| Peptic digest of animal tissue | 5.0 g |
| Beef extract | 1.0 g |
| Sodium chloride | 75.0 g |
| Phenol red | 0.025 g |
| Agar | 15.0 g |

A competent strain of *E. coli* HB101 produces blue colonies on LB (Luria-Bertani) medium supplemented with X-Gal (5-bromo-4chloro-3-indolyl-$\beta$-galactosidase), IPTG (isopropyl $\beta$-D-Thiogalactopyranoside). LB- medium contains Bacto tryptone, yeast extract, NaCl, agar and water.

Trypticase Soy Agar

Composition: Approximate formula per liter purified water

| | |
|---|---|
| Pancreatic digest of Casein | 15.0 g |
| Papaic digest of soybean meal | 5.0 g |
| Sodium chloride | 5.0 g |
| Agar | 15.0 g |

On this medium *Serratia marcescens* will produce red colonies.

The following enterobacterial species also produce pigments at a particular incubation temperature*:

| Organism | Colony color (temp. of incubation ° C.) | % pigmented |
|---|---|---|
| *Enterobacter agglomerans* | yellow | 76–89 |
| *Erwinia stewartii* | yellow (27) | 90–100 |
| *Escherichia hermannii* | yellow | 90–100 |
| *Xenorhabdus luminescens* | yellow, orange or red (25) | 90–100 |
| *Xenorhabdus poinarii* | Brown (25) | 90–100 |

*Manual of Clinical Microbiology, 6th ed. pp. 459

Still further certain medium with specific compounds or mixtures thereof will react or interact with enzyme metabolities elaborated by the growing bacteria and produce a visual color identifying the bacteria. Such compounds are disclosed in WO 97 39103, FR 2708286, FR 2708285 and WO 9409152 all by Alain Rambach. A typical medium having such a chromogen is exemplified below and can be obtained from CHROM agar Company, Paris, France in dehydrated powder form.

Composition:

Peptone

Meat extract

Yeast extract

Agar

Chromogen (a caprylic acid ester, specifically an indolyl caprylate) 40–200 mg/l On this medium Salmonella will produce blue colonies.

On CHROMagar orientation medium various bacteria will give different color of colonies. For example:

| | |
|---|---|
| *E. coli* | pink-red |
| *K. pneumoniae* | metallic blue |
| Enterobacter species | metallic blue |
| *Staph. aureus* | white to yellowish |
| *Citrobacter freudii* | metallic blue |
| Enterococcus species | turquoise |

(Ref. J. Clin. Microbiol. 36(4):990–994, 1998).

The results are assessed on the basis of the quantity of visually detectable bacteria on the medium—the lesser the number of visually detectable bacteria colonies on the medium, the more advantageous the inhibition of bacteria attachment composition while the greater the number of visually detectable bacteria colonies on the skin, the less advantageous the inhibition of bacteria attachment composition.

The term skin as used herein means the top layer of skin (i.e., stratum corneum) and all the components of the stratum, both cellular and acellular (i.e., biomolecules) such as proteins, carbohydrates, lipids and the like.

Any composition which can potentially or is known to inhibit the attachment of bacteria to skin can be evaluated by this method. In addition to the inhibition of bacteria attachment to skin compositions previously discussed are various compositions disclosed in U.S. provisional applications 60/087,533 and 60/087,532, both incorporated by reference. These compositions are directed to combinations including surfactant(s) with either a silicone such as dimethicone or a hydrocarbonaceous component such as petrolatum, minerol oil, paraffin and the like being present in attachment inhibiting amounts or both a silicone and a hydrocarbonaceous component together in attachment inhibiting amounts. A cationic polymer can also be present with either or both the silicone and hydrocarbonaceous component. Various other materials can also be present such as fragrance; antimicrobial materials such as Triclosan or trichlorocarbanilides; and the like. However, an antimicrobial material such as triclosan or triclocarban can be omitted as well.

This method can be used to compare and/or contrast known and unknown antibacteria attachment composition to each other or to a control composition.

The transference of bacteria to the skin can occur through any type of contact, for example skin to skin, or skin surface bearing such bacteria, for example doorknob, faucet, telephone, table top and the like. In sufficient density, bacteria can even be transferred to the skin in an airborne manner.

Transference of bacteria to the growth supporting medium from skin can occur through simple contact of the surface bearing the bacteria to the surface. An example of such a transfer is pressing a hand on the surface of an agar plate.

The bacteria are then allowed to grow into various colonies by incubating at a temperature optimum for bacterial growth and providing nutrients to the growth supporting medium, if not already present. After a period of time necessary to allow such bacteria to grow, at least partially dependent on temperature, pH, type of bacteria and the like, the bacteria are visualized without any assistance with any of the color including media, or compounds previously described. However, these additional method(s) of assisted visualization can be used, if desired.

Below are examples of the invention. These examples are intended to illustrate the broad nature of the invention and not be unduly restrictive thereof.

EXAMPLE 1

Thirty subjects participate in the studies. Subjects undergo a one-week washout period where they refrain from using any products labeled antibacterial such as antibacterial soaps, dishwashing liquids, lotions, creams, talcs, etc. and antidandruff shampoos for one week prior to the beginning of the study and for the duration of the test period.

On the day of the test, the subject's hands are rinsed with 70% ethanol to remove any contaminating bacteria and allowed to air dry. Each of the subject's hands are washed either four times or once by a technician. The washing procedure consists of a 15 second wash with the bar soap, 45 second lather with the gloved hand and 10 second rinse under running warm tap water. For multiple washes, the hands are allowed to air dry before proceeding with the next wash.

The subjects gently place each of their hands on the surface of a plastic plate previously contaminated with 200 $\mu l$ (approximately $10^6$) of the marker bacteria, Serratia marcescens (ATCC 14756). Two objects weighing approximately a total of 480 g are placed on top of the hands to help provide even pressure. The hands are left on the plate for 5 seconds. The subjects then, as soon as possible, gently place each of their hands on a pre-poured Microbial Content Agar hand imprint plate to transfer the bacteria. A technician applies gentle pressure to each of the subject's hands and fingers for 10 seconds. The same objects used as weights above are placed on top of the hands to help provide even pressure and the hands are left on the agar plate for 30 seconds. The subjects hands are decontaminated by soaking them in 70% isopropanol for 3 minutes.

The agar plates are incubated overnight at 35–37° C. The plates are evaluated by three judges using the following scale:

0—no bacterial growth
1—very slight bacterial growth
2—slight bacterial growth
3—moderate bacterial growth
4—strong bacterial growth
5—very strong bacterial growth
6—extreme bacterial growth Only pink colonies were evaluated. Half scores were allowed to delineate between whole unit scores.

The 3 judges scores for each plate are averaged. A paired t-test is employed using the judge average scores to determine whether significant references existed between products at the 5% significance level.

TABLE I

Bacteria Pick-Up Evaluation: Test Product vs. Placebo

| | Means Judges Score ± S.D. (n = 15 for each study) | |
|---|---|---|
| | 4 Washes | 1 Wash |
| Placebo[a] | 3.9 ± 1.0 | 3.5 ± 1.0 |
| Test Product[b] | 2.8 ± 1.0 | 2.0 ± 0.8 |
| p-value | ≦0.05 | ≦0.05 |

[a]Soap 77.5 wt %, free fatty acid 9.5 wt %, water 8.4 wt %.
[b]Soap 74.3 wt %, free fatty acid 9.2 wt %, polyquat 60.12 wt %, triclocarban 0.25 wt %, petrolatum 3.5 wt. %, dimethicone 0.1 wt. %, water 8.3 wt %.

As shown by the data, the test product has significantly inhibited the attachment of bacteria to the skin.

What is claimed is:

1. A method for visually demonstrating the effectiveness of an anti-bacteria attachment composition which comprises:

(a) treating skin with potential or known anti-bacteria attachment compositions;
   (b) contacting the said skin with a bacteria, resulting in the skin having bacteria attached to it;
   (c) contacting the skin with a bacteria growth supporting medium having optionally therein or later optionally added a compound or mixture thereof which will assist in visually detecting a bacterial colony wherein a composition of unknown anti-bacteria attachment effect is compared to a composition of known anti-bacteria attachment effect.

2. A method for visually demonstrating the effectiveness of an anti-bacteria attachment composition which comprises:

(a) treating skin with potential or known anti-bacteria attachment compositions;
   (b) contacting the said skin with a bacteria, resulting in the skin having bacteria attached to it;
   (c) contacting the skin with a bacteria growth supporting medium having optionally therein or later optionally added a compound or mixture thereof which will assist in visually detecting a bacterial colony wherein said bacteria is selected from the group consisting of *stapylococcus epidermis, staphylococcus aureus, corynebacterium minutissimum, escherichia coli, salmonella choleraesuis* and *serratia marcescens*.

3. The method of claim 2 wherein a cationic polymer is present in the composition.

4. The method of claim 3 wherein a surfactant is present in the composition.

5. The method of claim 4 wherein the composition also has an effective amount of an antimicrobial compound.

6. The method of claim 5 wherein the antimicrobial compound is triclosan or a trichloro-carbamilide.

7. The method of claim 4 wherein there is an antibacterial attachment effective amount of a material selected from the group consisting of a silicone, a hydrocarbonaceous compound and mixture thereof present in the composition.

8. A method for visually demonstrating the effectiveness of an anti-bacteria attachment composition which comprises:

(a) treating skin with potential or known anti-bacteria attachment compositions;
(b) contacting the said skin with a bacteria, resulting in the skin having bacteria attached to it;
(c) contacting the skin with a bacteria growth supporting medium having optionally therein or later optionally added a compound or mixture thereof which will assist in visually detecting a bacterial colony wherein there is an antibacterial effective amount of a material selected from the group consisting of a silicone, a hydrocarbonaceous compound and mixture thereof present in the composition.

9. The method of claim 8 wherein a cationic polymer is present in the composition.

10. The method of claim 9 wherein an effective amount of an antimicrobial compound is present in the composition.

* * * * *